(12) United States Patent
Meskens (10) Patent No.: US 9,227,058 B2
(45) Date of Patent: Jan. 5, 2016

(54) DATA/POWER TRANSFER OVER A COMMUNICATION LINK

(71) Applicant: Cochlear Limited, Macquarie University (AU)

(72) Inventor: Werner Meskens, Opwijk (BE)

(73) Assignee: Cochlear Limited, Macquarie University (AU)

( * ) Notice: Subject to any disclaimer, the term of this patent is extended or adjusted under 35 U.S.C. 154(b) by 497 days.

(21) Appl. No.: 13/691,203

(22) Filed: Nov. 30, 2012

(65) Prior Publication Data

US 2014/0155686 A1    Jun. 5, 2014

(51) Int. Cl.
*A61N 1/36*      (2006.01)
*A61N 1/372*    (2006.01)

(52) U.S. Cl.
CPC ........ *A61N 1/36032* (2013.01); *A61N 1/37252* (2013.01); *A61N 1/3727* (2013.01)

(58) Field of Classification Search
CPC ........... A61N 1/36032; A61N 1/37252; A61N 1/3727
See application file for complete search history.

(56) References Cited

U.S. PATENT DOCUMENTS

| | | | |
|---|---|---|---|
| 5,741,314 | A | 4/1998 | Daly et al. |
| 7,751,902 | B1 | 7/2010 | Karunasiri |
| 2011/0112611 | A1* | 5/2011 | Aghassian ............ 607/60 |

FOREIGN PATENT DOCUMENTS

| | | |
|---|---|---|
| WO | 2005110530 A2 | 11/2005 |
| WO | 2007124325 A2 | 11/2007 |

OTHER PUBLICATIONS

Guofeng, Li et al., "A Low Power Automatic Gain Control Loop for a Receiver," Journal of Semiconductors, Sep. 2010, vol. 31, No. 9, Chinese Institute of Electronics.

Zhou, Yanping et al., "A Wideband OOK Receiver for Wireless Capsule Endoscope," Proceedings of the 39th European Microwave Conference, Sep. 29-Oct. 1, 2009, p. 330-333, Rome, Italy.

Nehal, Qaiser "Design of a Wideband Variable Gain Amplifier," School of Electrical Engineering, Thesis submitted for examination for the degree of Master of Science in Technology, Nov. 4, 2011, Alto University School of Electrical Engineering.

Chi, Baoyong et al., "A Fast-Settling Wideband-IF ASK Baseband Circuit for a Wireless Endoscope Capsule," IEEE Transactions on Circuits and Systems—II: Express Briefs, vol. 56, No. 4, Apr. 2009, pp. 275-279.

(Continued)

*Primary Examiner* — Mark W Bockelman
(74) *Attorney, Agent, or Firm* — McDonnell Boehnen Hulbert & Berghoff LLP (57) ABSTRACT

The present application discloses systems, methods, and articles of manufacture for transferring data and/or data over a communication link. A medical device in one example includes receiver(s) configured to receive first signals, which include power signals and first stimulation data, and second signals, which include second stimulation data. Each of the first stimulation data and the second stimulation data includes data encoded according to a same data encoding protocol. The device also includes control circuitry coupled to the one or more receivers and configured to operate in a first mode and in a second mode. The control circuitry is configured in the first mode to apply the power signals to provide power to the medical device and to apply the first stimulation data to a medical device recipient. Further, the control circuitry is configured in the second mode to apply the second stimulation data to the medical device recipient.

14 Claims, 6 Drawing Sheets

(56) References Cited

OTHER PUBLICATIONS

Kim, Kihyun et al, "Design of OOK System for Wireless Capsule Endoscopy," Circuits and Systems (ISCAS), Proceedings of 2012 IEEE International Symposium, May 30, 2010-Jun. 2, 2010, pp. 1205-1208, Paris.

Wang, Xiaoman et al., "A Low-Power High-Data-Rate ASK IF Receiver with a Digital-Control AGC Loop," IEEE Transactions on Circuits and Systems—II: Express Briefs, vol. 57, No. 8, Aug. 2012, pp. 617-621.

* cited by examiner

DATA/POWER TRANSFER OVER A COMMUNICATION LINK

BACKGROUND

Various types of hearing prostheses provide persons with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound and a vibration mechanism to apply vibrations corresponding to the detected sound directly or indirectly to a person's bone or teeth, thereby causing vibrations in the person's inner ear and bypassing the person's auditory canal and middle ear. Vibration-based hearing devices include, for example, bone anchored devices, direct acoustic cochlear stimulation devices, or other vibration-based devices. A bone-anchored device typically utilizes a surgically implanted mechanism or a passive connection through the skin or teeth to transmit vibrations corresponding to sound via the skull. A direct acoustic cochlear stimulation device also typically utilizes a surgically implanted mechanism to transmit vibrations corresponding to sound, but bypasses the skull and more directly stimulates the inner ear. Other non-surgical vibration-based hearing devices may use similar vibration mechanisms to transmit sound via direct or indirect vibration of teeth or other cranial or facial bones or structures.

Persons with certain forms of sensorineural hearing loss may benefit from prostheses, such as cochlear implants and/or auditory brainstem implants. For example, cochlear implants can provide a person having sensorineural hearing loss with the ability to perceive sound by stimulating the person's auditory nerve via an array of electrodes implanted in the person's cochlea. A component of the cochlear implant detects sound waves, which are converted into a series of electrical stimulation signals that are delivered to the implant recipient's cochlea via the array of electrodes. Auditory brainstem implants can use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound. Further, some persons may benefit from hearing prosthesis that combine one or more characteristics of the acoustic hearing aids, vibration-based hearing devices, cochlear implants, and auditory brainstem implants to enable the person to perceive sound.

Some hearing prostheses include separate units or elements that function together to enable the person to perceive sound. In one example, a hearing prosthesis includes a first element that can be external to the recipient and a second element that can be implanted in the recipient. In the present example, the first element is configured to detect sound, to encode the detected sound as acoustic stimulation signals or data, to deliver the acoustic stimulation signals to the second element over a coupling or communication link between the first and second elements, and/or to deliver power to the second element over the link. The second element is configured to apply the delivered acoustic stimulation signals as output signals to the person's hearing system and/or to apply the delivered power to one or more components of the second element. The output signals applied to the person's hearing system can include, for example, audible signals, vibrations, and electrical signals, as described generally above.

The coupling or communication link between the first and second elements can be a radio frequency (RF) link operating in the magnetic or electric near-field, for example. As described generally above, the communication link can be utilized to deliver data and/or power between the elements of some hearing prostheses. Generally, it is desirable to improve on these communication links and related systems and methods or at least to provide one or more useful alternatives.

SUMMARY

The present disclosure relates to communication links and related systems and methods for transmitting power and/or data between devices. In one example, the communication link is configured to transfer data signals with or without power signals. Further, in various non-limiting examples, the communication link can be implemented in a hearing prosthesis, such as a cochlear implant, a bone anchored device, a direct acoustic cochlear stimulation device, an auditory brain stem implant, an acoustic hearing aid, or any other type of hearing prosthesis configured to assist a recipient in perceiving sound. However, the concepts disclosed herein can also applicable to a wide variety of medical and non-medical devices.

One example of the present disclosure is directed generally to a device configured to receive data and/or power over a communication link. In the present example, the device is configured to operate in a first mode and a second mode. In the first mode, the device receives data signals and power signals over the communication link and, in the second mode, the device receives data signals over the communication link. In both the first and second modes, the data signals received while the device operates in the first and second modes are encoded by the same data encoding protocol.

DETAILED DESCRIPTION

The following detailed description describes various features, functions, and attributes with reference to the accompanying figures. In the figures, similar symbols typically identify similar components, unless context dictates otherwise. The illustrative embodiments described herein are not meant to be limiting. Certain features, functions, and attributes disclosed herein can be arranged and combined in a variety of different configurations, all of which are contemplated in the present disclosure.

For illustration purposes, some features and functions are described with respect to hearing prostheses. However, various features and functions disclosed herein may be applicable to other types of types of devices, including other types of medical and non-medical devices.

Figure 1:
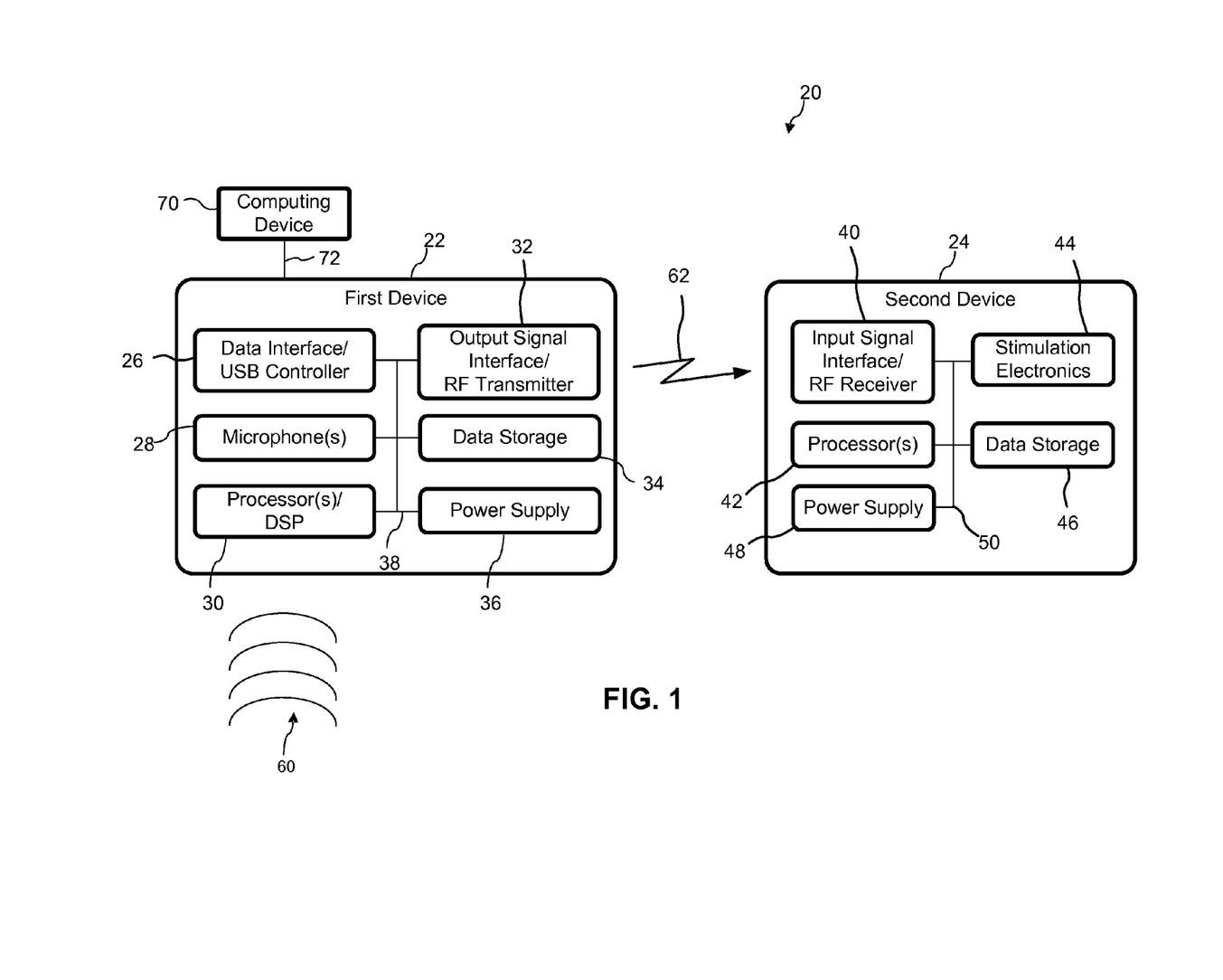
FIG. 1 illustrates a block diagram of a system according to an embodiment of the present disclosure.

Referring now to FIG. 1, an example hearing prosthesis system 20 includes a first device 22 and a second device 24. In various examples, the hearing prosthesis system 20 can be a cochlear implant, an acoustic hearing aid, a bone-anchored device, a direct acoustic cochlear stimulation device, an auditory brainstem implant, a hybrid hearing prosthesis, or any other type of hearing prosthesis configured to assist a prosthesis recipient in perceiving sound. To provide some non-limiting context to this description, the first device 22 can be generally external to a recipient and communicate with the second device 24 which can be implanted in the recipient. Although, in other examples, the devices 22, 24 can both be at least partially implanted or can both be at least partially external to the recipient.

The first device 22 illustrated in FIG. 1 includes a data interface or controller 26 (such as a universal serial bus (USB) controller), one or more microphones 28, one or more processors 30 (such as digital signal processors (DSPs)), an output signal interface or radio frequency (RF) transmitter 32, data storage 34, and a power supply 36 all of which are illustrated as being coupled directly or indirectly via a wired or wireless link 38. In the example of FIG. 1, the second device 24 includes an input signal interface or RF receiver 40, one or more processors 42, stimulation electronics 44, data storage 46, and a power supply 48 all of which are illustrated as being coupled directly or indirectly via a wired or wireless link 50.

Generally, the microphone(s) 28 are configured to receive external acoustic signals 60. The microphone(s) 28 can include combinations of one or more omnidirectional or directional microphones that are configured to receive background sounds and/or to focus on sounds from a specific direction, such as generally in front of the prosthesis recipient. Alternatively or in conjunction, the first device 22 is configured to receive sound information from other sources, such as electronic sound information received via the controller 26.

The processor 30 of the first device 22 is configured to convert or encode the acoustic signals 60 (or other sound information) into encoded acoustic signals that are applied to the RF transmitter 32. In the present example, the RF transmitter 32 of the first device 22 is configured to transmit the encoded acoustic signals as output signals 62 to the RF receiver 40 of the second device 24 over an inductive RF link using magnetically coupled coils. Thus, the output signal interface 32 can include an RF inductive transmitter system or circuit. Such an RF inductive transmitter system may further include an RF modulator, a transmitting coil, and associated circuitry for driving the coil to radiate the output signals 62 as RF signals. Illustratively, the RF link can be an On-Off Keying (OOK) modulated 5 MHz RF link, although other forms of modulation and signal frequencies can be used in other examples.

As mentioned above, the processor 30 converts the acoustic signals 60 into encoded acoustic signals that are transmitted as the output signals 62 to the RF receiver 40. More particularly, the processor 30 utilizes configuration settings, auditory processing algorithms, and a communication protocol to convert the acoustic signals 60 into acoustic stimulation data that is included in the output signals 62. One or more of the configuration settings, auditory processing algorithms, and communication protocol information can be stored in the data storage 34. Illustratively, the auditory processing algorithms may utilize one or more of speech algorithms, filter components, or audio compression techniques. Alternatively or in addition, the output signals 62 can include power signals that are used to supply power to one or more components of the second device 24.

In the context of a hearing implant, such as a cochlear implant, the acoustic stimulation data can define one or more of an intended cochlear implant electrode, mode of stimulation, stimulation amplitude, and stimulation duration. Consequently, the acoustic stimulation data can be used to control the timing and intensity of auditory stimulation pulses that are applied to a recipient by the stimulation electronics 44 of the second device 24. Generally, the stimulation electronics 44 can include a transducer that provides auditory stimulation to the recipient through electrical nerve stimulation, audible sound production, or mechanical vibration of the cochlea, for example.

A recipient's configuration settings allow the hearing prosthesis 20 to be configured for or fitted to a particular recipient. Further, hearing prostheses that utilize electrical stimulation, such as cochlear implants, can use speech algorithms that may be implemented by the processor 30 to generate stimulation data from the acoustic signals 60. For these systems based upon electrode stimulation, such speech algorithms include, but are not limited to, Continuous Interleaved Sampling (CIS), Spectral PEAK Extraction (SPEAK), Advanced Combination Encoders (ACE), Fundamental Asynchronous Stimulus Timing (FAST), Simultaneous Analog Stimulation, MPS, Paired Pulsatile Sampler, Quadruple Pulsatile Sampler, Hybrid Analog Pulsatile, n-of-m, and HiRes. More particularly, SPEAK is a low rate strategy that can operate within the 250-500 Hz range, ACE is a combination of CIS and SPEAK, and FAST is a low-rate, asynchronous stimulation that is temporally locked to envelope peaks of the input. Other proprietary and non-proprietary speech algorithms are also possible. These algorithms provide information on a stimulation mode (e.g., monopolar or bipolar electrode), a target electrode(s), and an amplitude of stimulation pulse(s).

Other vibration-based hearing devices that apply acoustic stimulation data to a recipient through vibration mechanisms may use equalizers or filters to compensate for an amplitude response of the vibration mechanisms and to compensate for hearing loss of the recipient. In one example, the equalized acoustic stimulation data can be sampled and processed according to a communication protocol and provided to the RF receiver 40.

Generally, the communication protocol defines how the stimulation data is transmitted from the first device 22 to the second device 24. For example, the communication protocol can be an RF protocol that is applied after the stimulation data is generated to define how the stimulation data will be encoded in a structured signal frame format of the output signals 62.

Illustratively, the output signals 62 can be transmitted over an OOK modulated 5 MHz RF link and the communication protocol defines how the stimulation data will be encoded over the link. For example, the 5 MHz link can be divided into cycles, each of which is defined by a period of a 5 MHz carrier wave. In this example, the stimulation data is encoded in cells, which are in turn encoded using a number of cycles. For example, a digital "one" data cell can be represented by a "high" signal for 5 cycles or periods of 200 ns of the OOK modulated link and a digital "zero" data cell can be represented by a "low" signal or an absence of signal for 5 cycles or period of 200 ns of the OOK modulated link. Further, data bits of the stimulation data are encoded using cells by combining the cells into tokens. The use of tokens can be utilized to provide positive disparity (more on than off cycles) and to limit the number of consecutive zero bits. The communication protocol can also define frames, which are a combination of tokens. Cumulatively, the frames, tokens, cells, and cycles define the structured signal frame format for encoding the stimulation data.

In addition to the stimulation data, the communication protocol can define how power signals are supplied over the structured signal frame format to provide a more continuous power flow to the second device 24 to charge the power supply 48, for example. Illustratively, the structured signal format can include output signal data frames for the stimulation data and additional output signal power frames. In one example, the output signal power frames include pseudo-data to fill in partially a death time associated with the signal, which facilitates the more continuous power flow to the second device. However, in other examples, additional output signal power frames are not necessary to transmit a suitable power flow to the second device because there is a sufficient number of "one" data cells of the stimulation data to provide power and/or a carrier wave of the output signals 62 is sufficient to provide power to the second device.

The communication protocol can include non-proprietary or proprietary protocols that define how the stimulation data and/or power signals are encoded in the structured signal frame format. For example, a cochlear implant can use different proprietary RF protocols such as EMA (electrode, mode, and amplitude format) and SEMA (sync, electrode, mode, and amplitude format), which are utilized, for example, by Cochlear Limited of Macquarie University, Australia. Other examples are also possible.

Once the stimulation data and/or power signals are encoded using the communication protocol, the encoded stimulation data and/or power signals can be provided to the RF transmitter 32, which can include an RF modulator. The RF modulator can then modulate the encoded stimulation data and/or power signals with the carrier signal, e.g., a 5 MHz carrier signal, and the modulated 5 MHz carrier signal can then be transmitted over the RF link from the RF transmitter 32 to the RF receiver 40. In various examples, the modulations can include OOK or frequency-shift keying (FSK) modulations based on RF frequencies between about 100 kHz and 50 MHz.

The second device 24 receives the RF output signals 62 via the input signal interface 40. In one example, the input signal interface 40 includes an RF receiver system or circuit. The RF receiver system can include a receiving coil and associated circuitry for receiving RF signals, such as the output signals 62. When the output signals 62 include stimulation data, the output signals 62 can be processed by the processor 42 to decode and extract the stimulation data. Further, the processor 42 is configured to apply the stimulation data to the recipient via the stimulation electronics 44. In addition, when the output signals 62 include power signals, the processor 42 can apply the power signals to charge the power supply 48, for example. Generally, the processor 42 can decode the output signals 62 in accordance with the configuration settings and/or the RF protocol described above. These settings and data relating to the RF protocol can be stored in the data storage 46.

The stimulation electronics 44 can take various forms depending on the type of hearing prosthesis. Illustratively, in embodiments where the hearing prosthesis 20 is a direct acoustic cochlear stimulation (DACS) device, the microphone(s) 28 are configured to receive the acoustic signals 60 and the processor 30 is configured to analyze and encode the acoustic signals into the output signals 62. In this example, the output signals 62 are received by the RF receiver 40, processed by the processor 42, and applied to the DACS recipient's inner ear via the stimulation electronics 44 that, in the present example, includes or is otherwise connected to an auditory nerve stimulator to transmit sound via direct mechanical stimulation.

Similarly, for embodiments where the hearing prosthesis 20 is a bone anchored device, the microphone(s) 28 and the processor 30 are configured to receive, analyze, and encode acoustic signals 60 into the output signals 62. The output signals 62 are received by the RF receiver 40, processed by the processor 42, and applied to the bone anchored device recipient's skull via the stimulation electronics 44 that includes or is otherwise connected to an auditory vibrator to transmit sound via direct bone vibrations, for example.

In addition, for embodiments where the hearing prosthesis 20 is an auditory brain stem implant, the microphone(s) 28 and the processor 30 are configured to receive, analyze, and encode the acoustic signals 60 into the output signals 62. The output signals 62 are received by the RF receiver 40, processed by the processor 42, and applied to the auditory brain stem implant recipient's auditory nerve via the stimulation electronics 44 that, in the present example, includes or is otherwise connected to one or more electrodes.

Similarly, in embodiments where the hearing prosthesis 20 is a cochlear implant, the microphone(s) 28 and the processor 30 are configured to receive, analyze, and encode the external acoustic signals 60 into the output signals 62 that are received by the RF receiver 40, processed by the processor 42, and applied to an implant recipient's cochlea via the stimulation electronics 44. In this example, the stimulation electronics 44 includes or is otherwise connected to an array of electrodes.

In embodiments where the hearing prosthesis 20 is an acoustic hearing aid or a combination electric and acoustic hybrid hearing prosthesis, the microphone(s) 28 and the processor 30 are configured to receive, analyze, and encode acoustic signals 60 into output signals 62 that are applied to a recipient's ear via the stimulation electronics 44 comprising a speaker, for example.

In one example, power signals are also provided with the output signals 62. In this example, the input signal interface or RF receiver 40 and/or the processor 42 includes circuitry or is otherwise configured to provide the power signals to one or more components of the second device. Illustratively, the input signal interface 40 can provide the power signals to charge an implant battery of the power supply 48. As such, the system 20 generally operates in a first mode and a second mode. In the first mode, the first device 22 transmits stimulation signals and power signals to the second device. In the second mode, the first device 22 transmits only stimulation signals to the second device. In yet other modes, the first device 22 can transmit and/or receive other data to/from the second device 24. For example, the first device 22 can transmit configuration settings to the second device 22.

Referring now to the power supplies 36, 48, each power supply provides power to various components of the first and second devices 22, 24, respectively. The power supplies 36, 48 can be any suitable power supply, such as non-rechargeable or rechargeable batteries. In one example, one or more both of the power supplies 36, 48 are batteries that can be recharged wirelessly, such as through inductive charging. Generally, a wirelessly rechargeable battery facilitates complete subcutaneous implantation of the devices 22, 24 to provide fully or at least partially implantable prostheses. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined, or otherwise, associated with use of the prosthesis.

Referring again to the data storage 34, 46, these components generally include any suitable volatile and/or non-volatile storage components. Further, the data storage 34, 46 may include computer-readable program instructions and perhaps additional data. In some embodiments, the data storage 34, 46 stores data and instructions used to perform at least part of the herein-described methods and algorithms and/or at least part of the functionality of the systems described herein. Although, the data storage 34, 46 in FIG. 1 are illustrated as separate blocks, in some embodiments, the data storage can be incorporated into other components of the devices 22, 24, such as the processor(s) 30, 42, respectively.

The system 20 illustrated in FIG. 1 further includes a computing device 70 that is configured to be communicatively coupled to the first device 22 (and/or the second device 24) via a connection or link 72. The link 72 may be any suitable wired connection, such as an Ethernet cable, a Universal Serial Bus connection, a twisted pair wire, a coaxial cable, a fiber-optic link, or a similar physical connection, or any suitable wireless connection, such as Bluetooth, Wi-Fi, WiMAX, inductive or electromagnetic coupling or link, and the like.

In general, the computing device 70 and the link 72 are used to operate the hearing prosthesis 20 in various modes. In a first example, the computing device 70 and the link 72 are used to develop and/or load a recipient's configuration data on the hearing prosthesis 20, such as via the data interface 26. In another example, the computing device 70 and the link 72 are used to upload other program instructions and firmware upgrades, for example, to the hearing prosthesis 20. In yet other examples, the computing device 70 and the link 72 are used to deliver data (e.g., sound information) and/or power to the hearing prosthesis 20 to operate the components thereof and/or to charge one or more of the power supplies 36, 48. Still further, various other modes of operation of the prosthesis 20 can be implemented by utilizing the computing device 70 and the link 72.

The computing device 70 can further include various additional components, such as a processor and a power source. Further, the computing device 70 can include user interface or input/output devices, such as buttons, dials, a touch screen with a graphic user interface, and the like, that can be used to turn the prosthesis 20 on and off, adjust the volume, switch between one or more operating modes, adjust or fine tune the configuration data, etc. Thus, the computing device 70 can be utilized by the recipient or a third party, such as a guardian of a minor recipient or a health care professional, to control the hearing prosthesis 20.

Various modifications can be made to the system 20 illustrated in FIG. 1. For example, user interface or input/output devices can be incorporated into the first device 22. Further, the system 20 may include additional or fewer components arranged in any suitable manner. In some examples, the system 20 may include other components to process external audio signals, such as components that measure vibrations in the skull caused by audio signals and/or components that measure electrical outputs of portions of a person's hearing system in response to audio signals.

Additionally, depending on the type and design of the system 20, the illustrated components may be enclosed within a single operational unit or distributed across multiple operational units, for example, two or more internal units or an external unit and an internal unit. Generally, an internal unit can be hermetically sealed and adapted to be at least partially implanted in a person.

Figure 2:
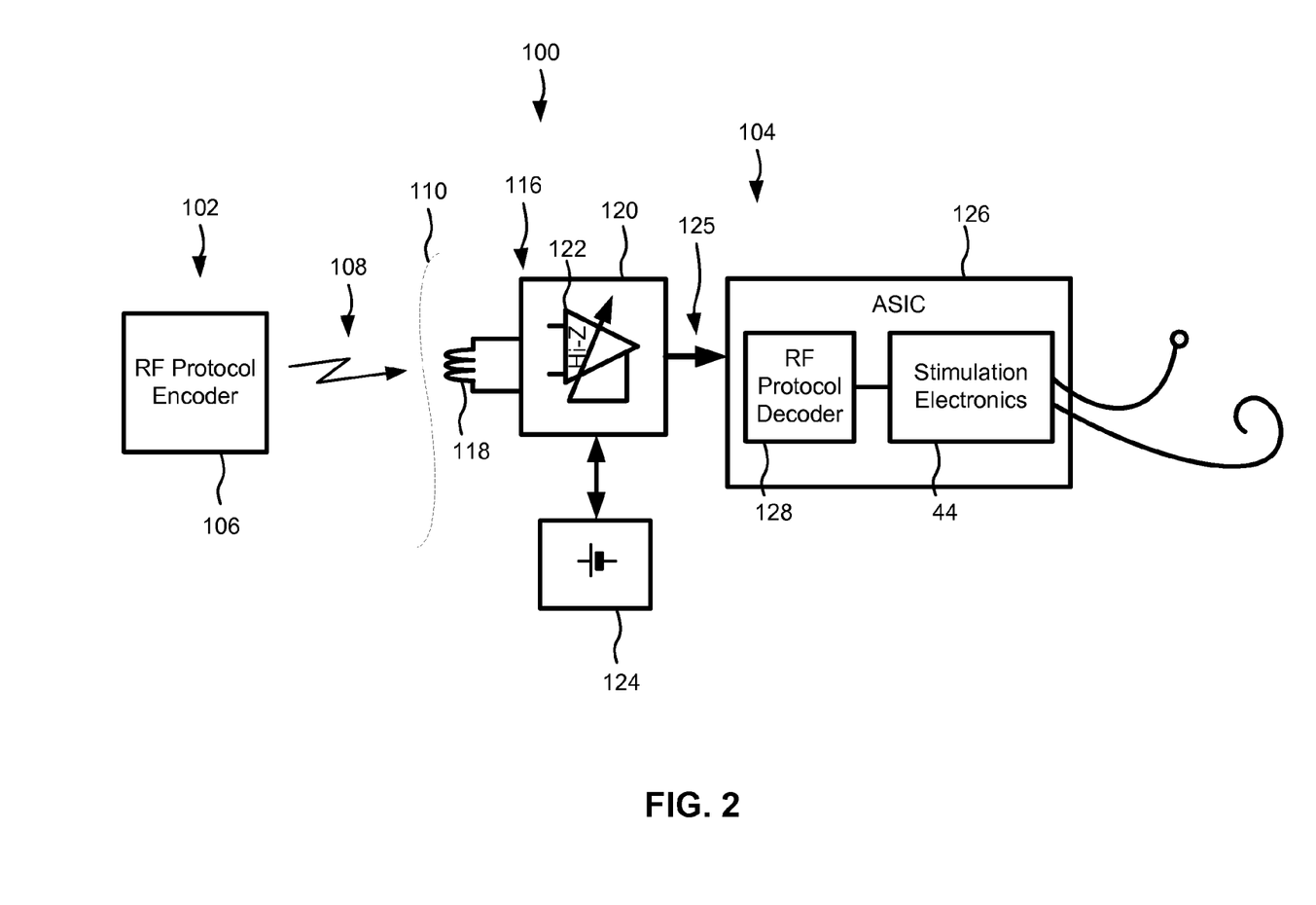
FIG. 2 illustrates a partial block, partial electrical schematic diagram of a system according to an embodiment of the present disclosure.

Referring now to FIG. 2, a partial block, partial electrical schematic diagram is illustrated of an example system 100, which includes various additional details of the hearing prosthesis of FIG. 1. In FIG. 2, the system 100 includes a first device 102 and a second device 104, which are similar to the first and second devices 22, 24 of FIG. 1, respectively, although not all of the various components of the devices are illustrated in FIG. 2. Illustratively, the first device 102 can be an external hearing prosthesis component and the second device 104 can be an implantable hearing prosthesis component. In the present example, the first device 102 includes an RF protocol encoder 106, which can be implemented by one or more components of the first device 22 of FIG. 1, such as the processor 30, the output signal interface 32, and the data storage 34. Generally, the first device 102 processes acoustic signals (e.g., the signals 60 of FIG. 1 or other sound information), converts the acoustic signals into stimulation data, and encodes the stimulation data into output signals 108 (e.g., similar to the output signals 62 of FIG. 1). More particularly, in the present example, the RF protocol encoder 106 encodes the stimulation data into the output signals 108. As described above, the output signals 108 can then be transmitted to the second device 104 by an RF transmitter (not shown). In the present example, the output signals 108 are transmitted from the first device 102 through a recipient's skin 110 to the second device 104.

As discussed generally above, the output signal interface 32 of FIG. 1 can be utilized to transmit the output signals 108 to the second device 104. Further, the output signals 108 include stimulation data that can be applied to a recipient through the stimulation electronics 44. The output signals 108 can also provide power to various components of the second device 104. For example, the output signals 108 can be encoded with additional output signal power frames to provide a more continuous power flow to components of the second device 104. Although, generally power can be extracted from the output signals 108 with or without additional output signal power frames. In the present example, the RF protocol encoder 106 encodes the stimulation data of the output signals 108 using the same RF protocol for providing stimulation data and extracting power, as well as, for providing only stimulation data. Such RF protocol can include any suitable communication protocol, such as any of the example protocols discussed hereinabove.

In FIG. 2, similarly to FIG. 1, an input signal interface 116 of the second device 104 receives the output signals 108. FIG. 2 illustrates some example components of the input signal interface 116, including a receiving coil 118 coupled to a block 120. In the present example, the block 120 includes a variable gain amplifier (VGA) 122. Further, FIG. 2 illustrates a rechargeable power supply 124 coupled to the block 120. Alternatively or in conjunction, the power supply 124 can be coupled to an application specific integrated circuit (ASIC) 126 of the second device 104.

The VGA 122 can be utilized to amplify the output signals 108 and provide output signals 125 from the block 120 that are at constant levels and independent of the incoming levels of the output signals 108. In the present example, the stable RF signals 125 are provided to the ASIC 126, which includes an RF protocol decoder 128 and stimulation electronics 44, as will be described in more detail hereinafter. Generally, the stable RF signals 125 are supplied to the ASIC 126 and the RF protocol decoder 128 to guarantee a robust operation of these components that is independent of magnetic field variation related to a distance between the first device 102 and the second device 104. Further, a control signal of the VGA 122 keeps the output of the VGA constant and may well be used to demodulate any RF signal using an OOK scheme.

Generally, in a first operating mode, the input signal interface 116 is configured to receive only the stimulation data of the output signals 108 from the first device 102. In this operating mode, the second device 104 may amplify the output signals 108 with the VGA 122, as needed, and apply the amplified output signals to the RF protocol decoder 128 of the second device 104. Further, in this operating mode, the rechargeable power supply 124 of the second device 104 provides power to different components thereof, such as the VGA 122, the RF protocol decoder 128, and the stimulation electronics 44. A gain setting of the VGA 122 can be varied depending on a coupled coil distance between the first device 102 and the second device 104.

In a second operating mode, power from the output signals 108 is applied to charge the power supply 124 and/or to provide power to other components of the second device 104. In this second operating mode, the output signals 108 can be used to provide power to the second device 104 and also to encode stimulation data that is decoded by the RF protocol decoder 128 and applied to a recipient through the stimulation electronics 44. Further, in the second operating mode, the gain setting of the VGA 122 may be about unity or less since the coupled coil distance between the first device 102 and the second device 104 is generally small to allow for good power transfer efficiency.

The ASIC 126 can be implemented by one or more components of the second device 22 of FIG. 1, such as the processor 42, the stimulation electronics 44, and the data storage 46. In other examples, the ASIC 126 can be implemented by a microcontroller, a processor, or one or more other discrete or integrated components. The RF protocol decoder 128 processes the stimulation data from the RF output signals 108 and extracts or otherwise processes the stimulation data for application to the recipient via the stimulation electronics 44.

In one embodiment, the stimulation data is encoded in the output signals 108 using the same RF protocol for both the first and second operating modes described above. Consequently, a single RF protocol encoder 106 can be used to encode the stimulation data in the output signals 108 for multiple operating modes. Further, since the VGA 122 provides the stimulation data in the output signals 125 at a constant power level to the ASIC 126, a single RF protocol decoder 128 can be utilized to decode the output signals 125 for multiple operating modes. A further benefit of using the same RF protocol for both the first and second operating modes is that other external or first devices 102 can be made compatible with the second device 104, which may already be implanted in a recipient and, therefore, not easily modified.

Figure 3:
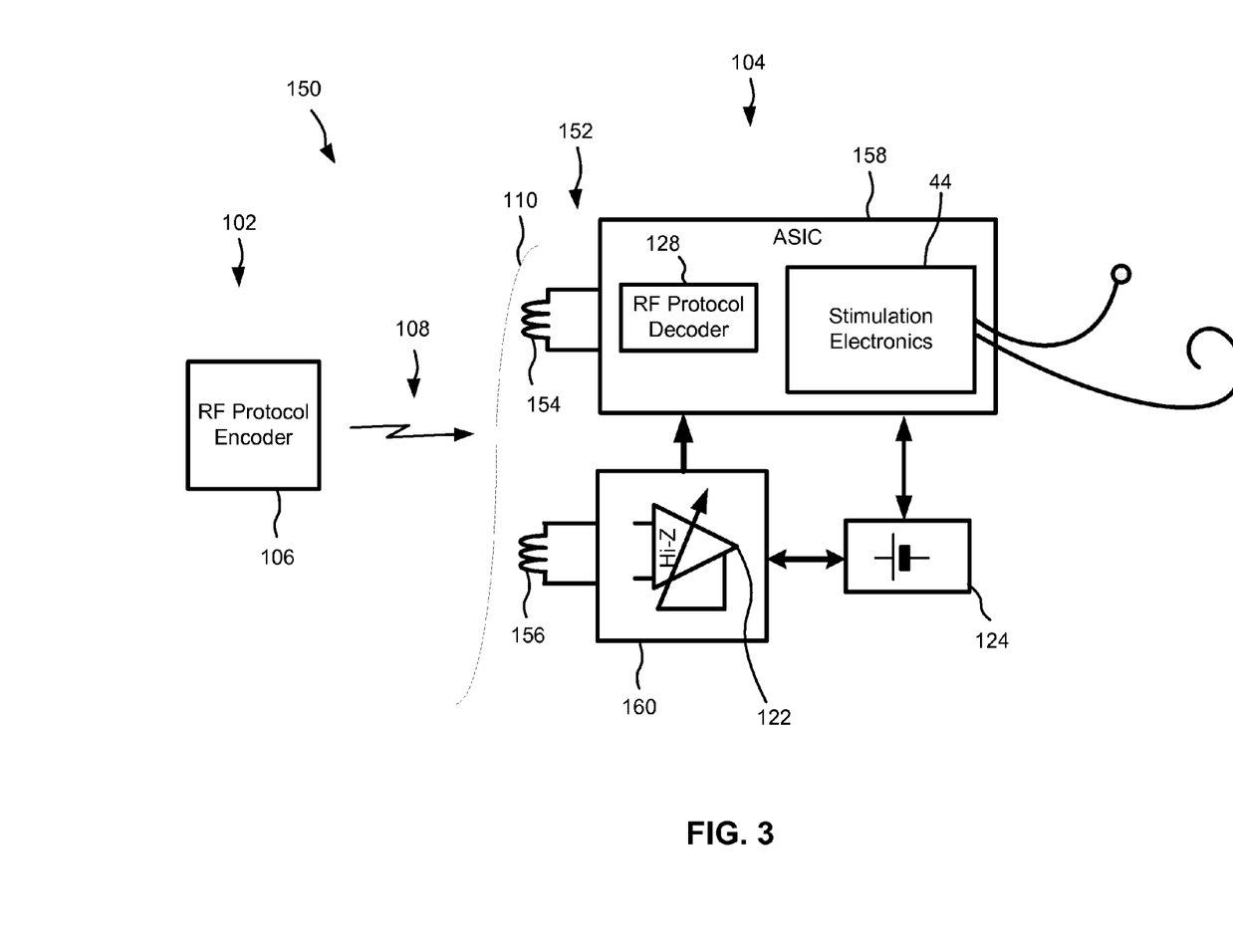
FIG. 3 illustrates a partial block, partial electrical schematic diagram of a system according to an embodiment of the present disclosure.

Referring now to FIG. 3, another system 150 is illustrated that is similar in form and function to the system 100 of FIG. 2, except that the system 150 includes an input signal interface 152 that includes a first receiver coil 154 and a second receiver coil 156. The first receiver coil 154 is coupled to an ASIC block 158, which in the present example further includes an RF protocol decoder 128 and stimulation electronics 44. The second receiver coil is coupled to a block 160, which includes a VGA 122. Further, a rechargeable power supply is coupled to the ASIC 158 and the block 160.

Generally, in use, the first device 102 processes acoustic signals (e.g., the signals 60 of FIG. 1 or other sound information), converts the acoustic signals into stimulation data, and the RF protocol encoder 106 encodes the stimulation data into output signals 108 (e.g., the output signals 62 of FIG. 1). The output signals 108 can then be transmitted to the second device 104 by an RF transmitter, such as the RF transmitter 32 of FIG. 1.

As described above with reference to FIG. 2, the output signals 108 include stimulation data and facilitate a substantially continuous transfer of power signals to the second device 104. In the present example, in a first operating mode, the output signals 108 are received by the first receiver coil 154, which applies the stimulation data of the output signals to the ASIC 158 and applies the output signals to provide power to one or more components of the second device 104. In the first operating mode, the output signals 108 can be encoded with additional output signal power frames to provide a more continuous power flow to components of the second device 104. Although, generally power can be extracted from the output signals 108 with or without additional output signal power frames. Further, in use, the first receiver coil 154 can be very closely coupled to an RF transmitter coil, for example, the coils can be within about 16 mm from one another.

Further, in a second operating mode, the second output signals 108 are received by the second receiver coil 156, which amplifies the stimulation data of the output signals using the VGA 122 and applies the amplified stimulation data to the ASIC 158. The RF protocol decoder 128 of the ASIC 158 processes the stimulation data and extracts or otherwise processes the stimulation data for application to the recipient via the stimulation electronics 44. In one example, the second receiver coil 156 can be relatively weakly coupled to an RF transmitter coil and practically spaced up to 30 cm from the transmitter coil. In both operating modes, the stimulation data can be encoded in the output signals 108 using the same RF protocol encoder 106.

Figure 4:
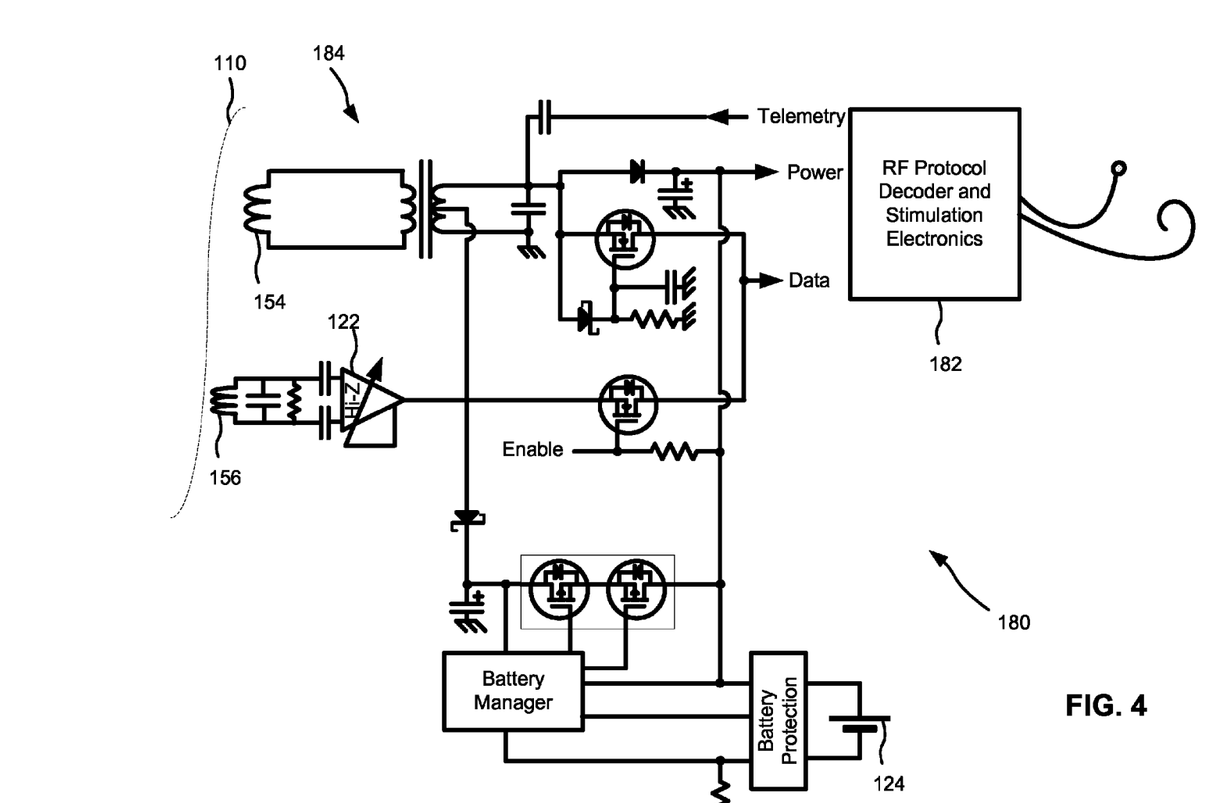
FIG. 4 illustrates a partial block, partial electrical schematic diagram of a device according to an embodiment of the present disclosure.

FIG. 4 illustrates another device 180, which is similar to the first device 104 of FIG. 3, and includes a first receiver coil 154 and a second receiver coil 156. The device 180 also includes a VGA 122, a power supply 124, and a block 182, which represents an RF protocol decoder and stimulation electronics. FIG. 4 also illustrates additional electrical components, including circuitry 184 (e.g., transformers, transistor switches, diodes, capacitors, resistors, etc.) coupled to the first and second coils 154, 156 and configured to deliver the stimulation data and/or the power signals of output signals received from another device (e.g., the output signals 62, 108) to the appropriate components, as described above. It should be understood, however, that the device 180 can take a variety of other forms, the specific details of which are not critical to an understanding of the present disclosure.

Figure 5:
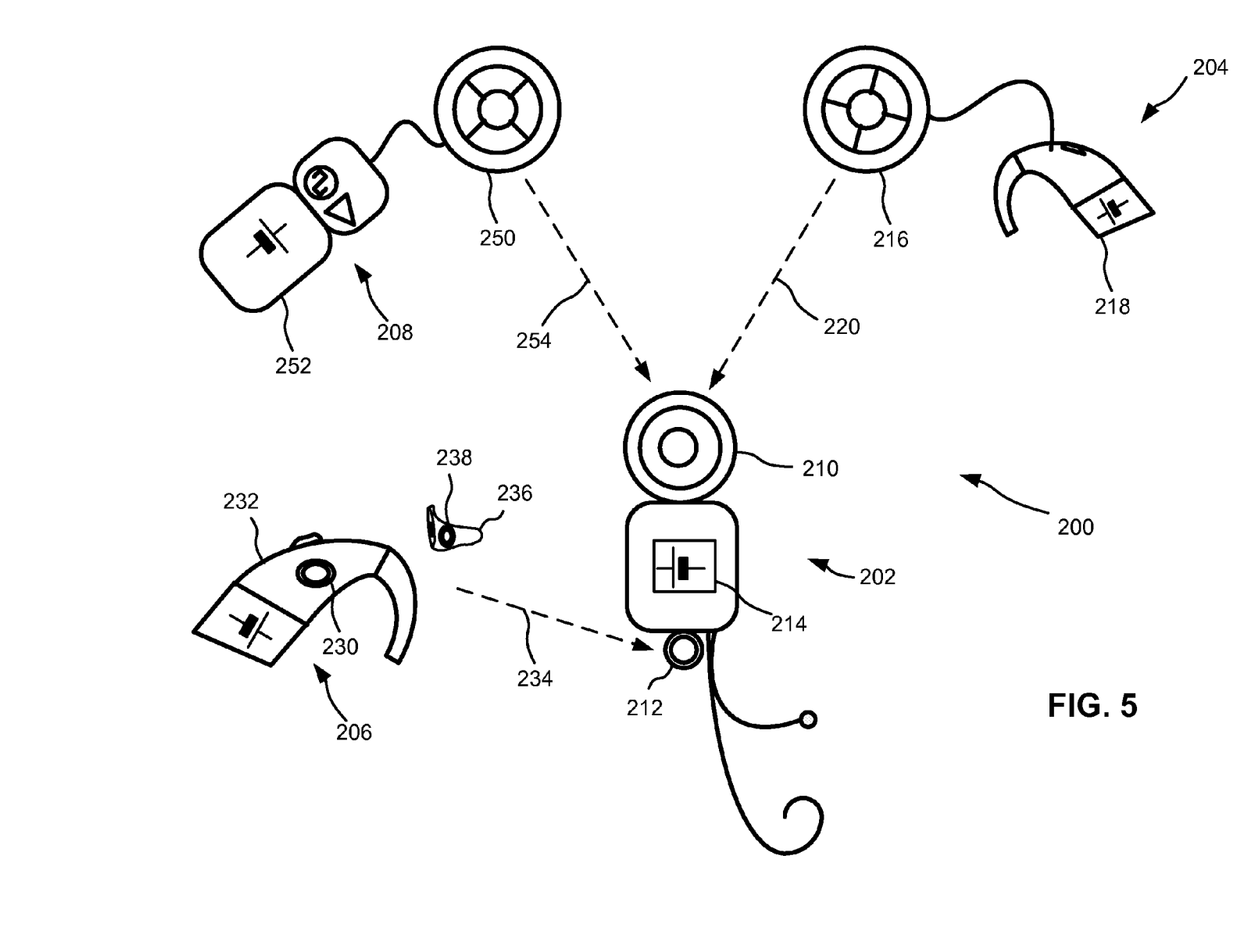
FIG. 5 illustrates a general block diagram of a system according to an embodiment of the present disclosure.

FIG. 5 illustrates various examples of the previously described system and devices, such as the system of FIG. 3. More particularly, in FIG. 5 a system 200 includes an implantable device 202, which can communicate with various external devices 204, 206, and 208. The implantable device 202 includes a first receiver coil 210, a second receiver coil 212, and a rechargeable power supply 214.

In a first configuration, the implantable device 202 communicates with the device 204, which includes a transmitter coil 216 coupled to a behind-the-ear (BTE) hearing prosthesis component 218. In this first configuration, the BTE component 218 transmits output signals 220 to the implantable device 202. More specifically, the transmitter coil 216 transmits the output signals 220, which include acoustic stimulation data and power signals, to the first receiver coil 210 of the implantable device 202.

In a second configuration, the implantable device 202 communicates with the device 206, which includes a transmitter coil 230 coupled to a (BTE) hearing prosthesis component 232. In this second configuration, the BTE component 232 transmits output signals 234 to the implantable device 202. More specifically, the transmitter coil 230 transmits the output signals 234, which include acoustic stimulation data, to the second receiver coil 212 of the implantable device 202. Alternative or in conjunction, in the second configuration, the device 206 can include an in-the-ear component 236, which further includes a transmitter coil 238. In this example, the transmitter coil 238 is configured to transmit the output signals 234 to the second receiver coil 212 of the implantable device 202.

In a third configuration, the implantable device 202 communicates with the device 208, which includes a transmitter coil 250 coupled to a battery charger 252. In this third configuration, the battery charger 252 transmits output signals 254 to the implantable device 202. More specifically, the transmitter coil 250 transmits the output signals 254, which include power signals, to the first receiver coil 210 of the implantable device 202.

In all three configurations, a same RF protocol can be used to encode stimulation data into the output signals.

Figure 6:
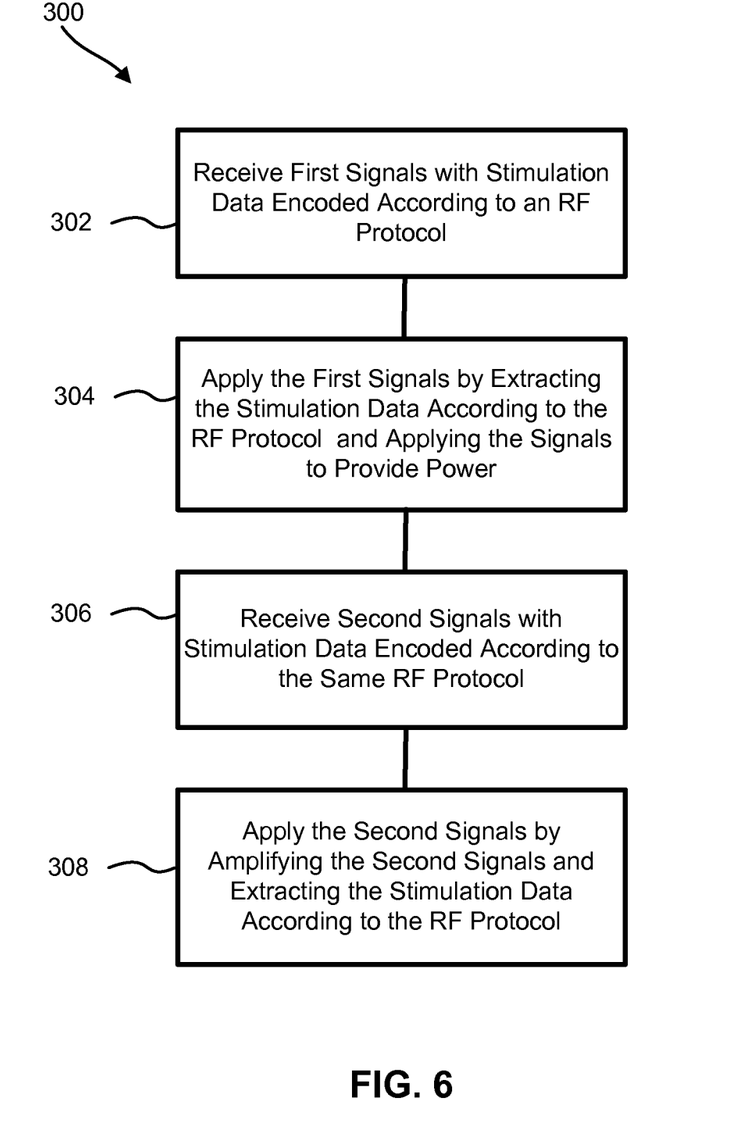
FIG. 6 illustrates a flowchart showing a method for applying different output signals according to an embodiment.

Referring now to FIG. 6, an example method 300 is illustrated, which can be implemented by the systems and devices described hereinabove. Generally, the method 300 may include one or more operations, functions, or actions as illustrated by one or more of blocks 302-308. Although the blocks 302-308 are illustrated in a sequential order, the blocks may also be performed in parallel, and/or in a different order than described herein. The method 300 may also include additional or fewer blocks, as needed or desired. For example, the various blocks 302-308 can be combined into fewer blocks, divided into additional blocks, and/or removed based upon a desired implementation.

In addition, each block 302-308 may represent a module, a segment, or a portion of program code, which includes one or more instructions executable by a processor for implementing specific logical functions or steps in the process. The program code may be stored on any type of computer readable medium or storage device including a disk or hard drive, for example. The computer readable medium may include non-transitory computer readable medium, such as computer-readable media that stores data for short periods of time like register memory, processor cache, and Random Access Memory (RAM). The computer readable medium may also include non-transitory media, such as secondary or persistent long term storage, like read only memory (ROM), optical or magnetic disks, compact-disc read only memory (CD-ROM), etc. The computer readable media may also include any other volatile or non-volatile storage systems. The computer readable medium may be considered a computer readable storage medium, for example, or a tangible storage device. In addition, one or more of the blocks 302-308 may represent circuitry that is wired to perform the specific logical functions of the method 300.

In FIG. 6, at block 302, a device, such as an implantable device receives first output signals. These output signals include both stimulation data and power signals. More particularly, in one example, the stimulation data represents acoustic signals received from a microphone or from some other source. The acoustic signals are encoded into the stimulation data according to a speech algorithm and then the stimulation data can be encoded in the first output signals using an RF protocol.

At block 304, the device applies the first output signals, as described above. For example, the device processes the first output signals to extract the stimulation data and applies the stimulation data to the recipient via the stimulation electronics 44. The device can process the first output signals according to the RF protocol to extract the stimulation data. In the present example, the device also applies the power signals of the first output signals to charge a power supply.

At block 306, the device receives second output signals, which include stimulation data. In one example, the stimulation data in the second output signals represents acoustic signals received from a microphone or from some other source. As discussed above, these acoustic signals are encoded into the stimulation data according to a speech algorithm and then the stimulation data can be encoded in the second output signals using an RF protocol. Specifically, the same RF protocol used for the first output signals is used to encode the stimulation data for the second output signals.

At block 308, the device processes the second output signals to extract the stimulation data and applies the stimulation data to the recipient via the stimulation electronics 44. In one example, at block 308, the device processes the second output signals by amplifying the output signals using a VGA before applying the stimulation data to the recipient. Further, the device may process the second output signals according to the same RF protocol as the first output signals to extract the stimulation data.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:
1. A method comprising:
receiving, at a first coil of a hearing prosthesis, first radio frequency (RF) signals that include power signals and first auditory stimulation data that is encoded according to a data encoding protocol;
applying, through control circuitry associated with the hearing prosthesis, the power signals to provide power to the hearing prosthesis and the first auditory stimulation data to a hearing prosthesis recipient through stimulation electronics associated with the hearing prosthesis;
receiving, at a second coil of the hearing prosthesis, second RF signals that include second auditory stimulation data that is encoded according to the data encoding protocol;
applying, through the control circuitry, the second auditory stimulation data to the hearing prosthesis recipient through the stimulation electronics.
2. The method of claim 1, further comprising amplifying the second RF signals through a variable gain amplifier coupled to the second coil before applying the second auditory stimulation data to the hearing prosthesis recipient.

3. The method of claim 1, further comprising decoding the first auditory stimulation data, according to a data decoding protocol, before applying the first auditory stimulation data to the hearing prosthesis recipient, and decoding the second auditory stimulation data, according to the data decoding protocol, before applying the second auditory stimulation data to the hearing prosthesis recipient.

4. The method of claim 1, further comprising applying the power signals to charge a battery coupled to the control circuitry.

5. The method of claim 1, further comprising receiving the first RF signals and the second RF signals through a transcutaneous RF link.

6. The method of claim 1, further comprising receiving the first RF signals and the second RF signals from one or more of a headpiece coil, a behind-the-ear component, or an in-the-ear component.

7. The method of claim 1, wherein the stimulation electronics are connected to an auditory nerve stimulator or an auditory vibrator.

8. A hearing prosthesis system comprising:
a first receiver configured to wirelessly receive first signals including power signals and first auditory stimulation data;
a second receiver configured to wirelessly receive second signals including second auditory stimulation data, wherein the first and second auditory stimulation data are encoded by a same data encoding protocol;
an amplifier coupled to the second receiver; and
control circuitry coupled to the first receiver and to the amplifier, wherein the control circuitry is configured to operate in a first mode and in a second mode,
wherein the control circuitry is configured in the first mode to apply the power signals to provide power to the hearing prosthesis and to apply the first auditory stimulation data to a hearing prosthesis recipient through stimulation electronics coupled to the control circuitry, and
wherein the control circuitry is configured in the second mode to apply the second auditory stimulation data to the hearing prosthesis recipient through the stimulation electronics.

9. The system of claim 8, wherein the amplifier is a variable gain amplifier and the first and second receivers are coils.

10. The system of claim 8, wherein the first and second receivers, the amplifier, and the control circuitry are enclosed in a hermetically-sealed, implantable housing.

11. The system of claim 10, further comprising a separate component from the implantable housing, wherein the separate component includes one or more of a microphone, a sound processor, or a transmitter.

12. The system of claim 11, wherein the separate component includes one or more of a headpiece coil, a behind-the-ear component, or an in-the-ear component.

13. The system of claim 8, further comprising stimulation electronics coupled to the control circuitry, wherein the stimulation electronics are connected to an auditory nerve stimulator or an auditory vibrator.

14. The system of claim 8, further comprising battery charging circuitry coupled to the control circuitry, wherein the control circuitry is configured in the first mode to apply the power signals to the battery charging circuitry.

* * * * *